United States Patent
Lee et al.

(10) Patent No.: US 10,578,622 B2
(45) Date of Patent: Mar. 3, 2020

(54) SENSORS FOR DETECTING CITRATE, AND METHOD OF DETECTING CITRATE USING THE SAME

(71) Applicant: KOREA INSTITUTE OF SCIENCE AND TECHNOLOGY, Seoul (KR)

(72) Inventors: Kang Bong Lee, Seoul (KR); Yun Sik Nam, Seoul (KR); Kanagaraj Rajalakshmi, Seoul (KR); Muthusamy Selvaraj, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 155 days.

(21) Appl. No.: 15/994,494

(22) Filed: May 31, 2018

(65) Prior Publication Data

US 2018/0348229 A1 Dec. 6, 2018

(30) Foreign Application Priority Data

Jun. 1, 2017 (KR) ........................ 10-2017-0068454

(51) Int. Cl.
| | | |
|---|---|---|
| *G01N 33/58* | (2006.01) | |
| *C07F 5/02* | (2006.01) | |
| *G01N 33/574* | (2006.01) | |
| *G01N 33/52* | (2006.01) | |
| *G01N 33/84* | (2006.01) | |

(52) U.S. Cl.
CPC ........... *G01N 33/582* (2013.01); *C07F 5/025* (2013.01); *G01N 33/526* (2013.01); *G01N 33/57434* (2013.01); *G01N 33/84* (2013.01); *G01N 2800/347* (2013.01)

(58) Field of Classification Search
CPC .. C07F 5/025; G01N 2800/37; G01N 33/526; G01N 33/57434; G01N 33/582; G01N 33/84
See application file for complete search history.

(56) References Cited

U.S. PATENT DOCUMENTS

| | | |
|---|---|---|
| 8,808,565 B2 | 8/2014 | Han et al. |
| 2011/0046204 A1 | 2/2011 | Costello et al. |

FOREIGN PATENT DOCUMENTS

| | | |
|---|---|---|
| JP | 2014-41154 A | 3/2014 |
| JP | 2014-100100 A | 6/2014 |
| KR | 10-1348391 B1 | 1/2014 |
| KR | 10-2015-0069092 A | 6/2015 |
| KR | 10-1823114 B1 | 1/2018 |
| WO | WO 2009/026152 A1 | 2/2009 |

OTHER PUBLICATIONS

Subrao et al. Beilstein J. Org. Chem. (2015) 11: 233-241 (Year: 2015).*

Kamal et al., "Synthesis of 2-aryl-1,2,4-oxadiazolo-benzimidazoles: Tubulin polymerization inhibitors and apoptosis inducing agents," Bioorganic & Medicinal Chemistry 23 (2015) 4608-4623.

Kimura et al., "Development of Functional Imidazole Derivatives: A Potential Chemiluminescent Chemosensor," Bull. Chem. Soc. Jpn., 78, 929-931 (2005).

* cited by examiner

*Primary Examiner* — Susan M Hanley
(74) *Attorney, Agent, or Firm* — Birch, Stewart, Kolasch & Birch, LLP

(57) ABSTRACT

Disclosed is a citrate detection sensor including a compound represented by the Chemical Formula 1. The citrate detection sensor is bound specifically with citrate which is under-expressed specifically in cells, such as prostate cancer cells, to express a green fluorescence color. Thus, it is possible to detect citrate with ease by using the citrate detection sensor.

19 Claims, 14 Drawing Sheets

Concentration      0      0.2     0.4     0.6     0.8     1.0     1.2
of citrate (µM)

SENSORS FOR DETECTING CITRATE, AND METHOD OF DETECTING CITRATE USING THE SAME

CROSS-REFERENCE TO RELATED APPLICATION

This application claims priority to Korean Patent Application No. 10-2017-0068454, filed on Jun. 1, 2017, and all the benefits accruing therefrom under 35 U.S.C. § 119, the contents of which in its entirety are herein incorporated by reference.

BACKGROUND

1. Field

The present disclosure relates to a novel citrate detection sensor and a method for detecting citrate using the same. Particularly, the present disclosure relates to a citrate detection sensor using a novel compound and a method for detecting citrate using the same.

Description of State-Supported Research and Development

The present disclosure is made under the support of Ministry of Environment with the supervision of Korea Institute of Science and Technology (the research management specialized institute is Korea Environmental Industry & Technology Institute, the subject business title is "Development of Technology for Real Time In-Situ Detection of Bioaerosol and Harmful Heavy Metal Ingredients in Ultrafine Dust and Fine Dust", and the subject number is 1485014151).

2. Description of the Related Art

Development of a metal-free receptor molecular probe for detecting citrate anion in a physiological environment is still a challenging subject to those studying biosensors and medical science. Citrate is one of the most important target anions, since it plays an important role in a metabolic path of cells for transferring energy and synthesizing biomolecules in the Krebs cycle of a biological system.

Concentration of citrate in a biological fluid is used to diagnose a part of pathological conditions, such as kidney function disorders, kidney stone and glycogen storage. In other words, citrate concentration in the body fluid of a healthy man is in a normal range, 50-200 mM, but citrate concentration of a prostate cancer tissue is decreased to 2-20 mM, which suggests a significant degree of progress of prostate cancer. Thus, citrate concentration is decreased significantly in a patient suffering from prostate cancer. Therefore, monitoring citrate concentration from a small amount of body fluid sample provides a wide range of opportunities to screen prostate cancer at the initial stage thereof.

Recently, a fluorescence sensor has been used widely as novel technology in the field of detection of small molecules, cations and anions and analysis of biomolecules by virtue of high sensitivity and selectivity, in-situ visualization, easy handling and low cost.

Recently, a chemical fluorescence sensor using a disulfonated aluminum complex has been reported. It is capable of function as a sensor, since it is bound to citrate through a zinc-citrate coordinate bonding. Particularly, it is reported that the sensor can form a binuclear zinc complex to citrate through a zinc-citrate coordinate bonding. Herein, the main strategy is designed based on two-step indicator displacement assay (IDA).

Thus, the conventional chemical sensor to citrate most frequently appears as a complex, such as $Al^{3+}$, $Cu^{2+}$ and $Zn^{2+}$, since the complex metal ion has a vacant orbital for new coordination with citrate. It is possible for an IDA-type probe to detect citrate ion by using this.

However, such a chemical sensor forming a metal complex shows the following disadvantages when it reacts in a living biological organism: i) the IDA-type probe can detect citrate only when the binding affinity between citrate and a metal-complex probe is higher as compared to the binding between the complex probe and a metal or ligand. ii) Use of a metal-complex probe in a biological system may cause pathological diseases, such as Parkinson's disease and Alzheimer's disease. iii) Since the IDA-type probe indirectly detects citrate, it shows low sensitivity and low reaction rate.

Therefore, there is a need for developing a non-IDA type chemical sensor which allows direct one-step detection of citrate and is not bound with a metal ion that may be used for intracellular fluorescence imaging.

SUMMARY

The present disclosure is directed to providing a citrate detection sensor and a method for detecting citrate using the same.

In one aspect, there is provided a citrate detection sensor including a compound represented by the following Chemical Formula 1:

[Chemical Formula 1]

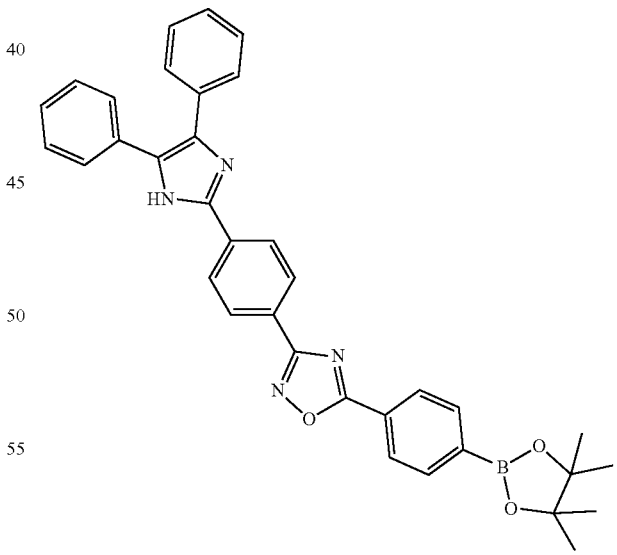

According to an embodiment, the compound represented by Chemical Formula 1 may express a green fluorescence color through the reaction with citrate.

According to another embodiment, when the compound represented by Chemical Formula 1 reacts with citrate, the fluorescence intensity in a wavelength range of 400-450 nm may be increased to 450-700 nm.

According to still another embodiment, the citrate detection sensor may have a pH controlled to 6-8.

According to still another embodiment, the citrate detection sensor is capable of detecting citrate at 20-37° C.

According to still another embodiment, the citrate detection sensor may provide a citrate detection result within 15 minutes.

According to still another embodiment, the citrate detection sensor may have a detection limit of 10 nM.

According to still another embodiment, the citrate detection sensor may be used to detect citrate in cells.

According to still another embodiment, the citrate detection sensor may be used to detect citrate in prostate cancer cells.

According to yet another embodiment, the citrate detection sensor may be a paper-strip type sensor including the compound represented by Chemical Formula 1 supported in paper.

In another aspect, there is provided a kit for diagnosing prostate cancer which includes a citrate detection sensor including a compound represented by the following Chemical Formula 1:

[Chemical Formula 1]

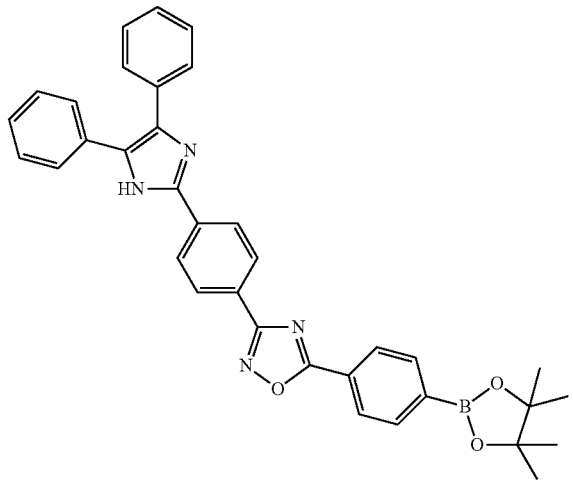

According to an embodiment, the kit for diagnosing prostate cancer may further include a unit for determining concentration in a biological sample isolated from the human body, wherein the unit for determining concentration in a biological sample may further include the citrate detection sensor.

According to another embodiment, the unit for determining concentration in a biological sample may further include instructions including a method for diagnosing prostate cancer, wherein the instructions may include a screening method of diagnosing prostate cancer or potential prostate cancer, when the citrate concentration in at least one of the body fluid and blood analyzed from the unit for determining concentration in a biological sample is reduced to less than 1/10 of the citrate concentration in the normal control.

According to still another embodiment, the unit for determining concentration in a biological sample may further include instructions including a method for diagnosing prostate cancer, wherein the instructions may include a screening method of diagnosing prostate cancer or potential prostate cancer, when the citrate detection sensor expresses blue fluorescence as compared to the normal control after the sensor reacts with at least one of the body fluid and blood analyzed from the unit for determining concentration in a biological sample.

In still another aspect, there is provided a method for detecting citrate which includes: preparing a citrate detection sensor including a compound represented by the following Chemical Formula 1; allowing the citrate detection sensor to react with a sample to be analyzed; and determining a change in fluorescence of the citrate detection sensor after the citrate detection sensor reacts with the sample to be analyzed to detect citrate:

[Chemical Formula 1]

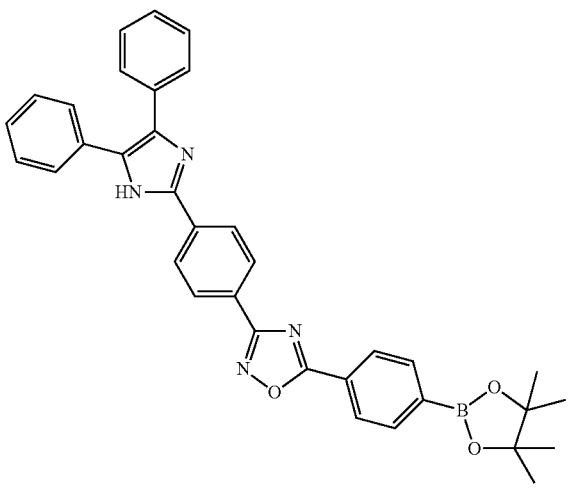

According to an embodiment, the allowing the sensor to react with the sample to be analyzed may include: introducing the sensor and the sample to be analyzed to a reaction chamber; controlling pH in the reaction chamber; and allowing the sensor to react with the sample to be analyzed in the reaction chamber.

According to another embodiment, pH in the reaction chamber may be controlled to 6-8.

According to still another embodiment, the sample to be analyzed may include at least one of the body fluid and blood in the human body.

According to yet another embodiment, the sample to be analyzed which reacts with the citrate detection sensor may include at least one of the body fluid and blood in prostate cancer cells.

In the citrate detection sensor according to an embodiment, a boronate moiety acts as a Lewis acid so that it may substitute for a metal complex when detecting citrate. Herein, the boron element present in the boronate moiety has a $sp^2$ hybrid orbital and an unoccupied 'p' orbital with a triangular planar structure which provide a new coordination site with citrate. Herein, the Lewis acidic boron element may function as a receptor for anions, such as fluoride ($F^-$), hydroxide ($OH^-$) and cyanide ($CN^-$).

Therefore, citrate may react as a Lewis base and donate electrons to the vacant 'p' orbital of boron (Lewis acidic) so that the $sp^2$-triangular plane may be converted into a $sp^3$-tetrahedral structure. In this case, fluorescence wavelength may be changed from blue fluorescence to green fluorescence through the reaction with citrate. As a result, it is possible to detect citrate with ease merely by the naked eyes and/or a fluorescence photometer.

In addition, the citrate detection sensor has significantly high selectivity and sensitivity to citrate, and thus detects citrate rapidly. Therefore, the citrate detection sensor may be used widely in various fields, such as pharmaceuticals, industrial spots handling chemicals, environmental pollution samples, forensic scientific samples and drinking water. Particularly, since the citrate detection sensor may be applied directly to living cells, it may be used with ease in prostate cancer cell lines in which citrate is under-expressed.

DETAILED DESCRIPTION

Exemplary embodiments now will be described more fully hereinafter with reference to the accompanying drawings. However, the following embodiments described with reference to the drawings are for illustrative purposes only and the scope and application of the present disclosure should not be construed as limited to the exemplary embodiments set forth therein.

As used herein, 'citrate detection sensor' covers not only a sensor detecting the presence/absence of citrate in a sample but also a concentration-determining sensor capable of determining the concentration of citrate in a sample.

Citrate Detection Sensor

In one aspect, there is provided a citrate detection sensor including a compound represented by the following Chemical Formula 1:

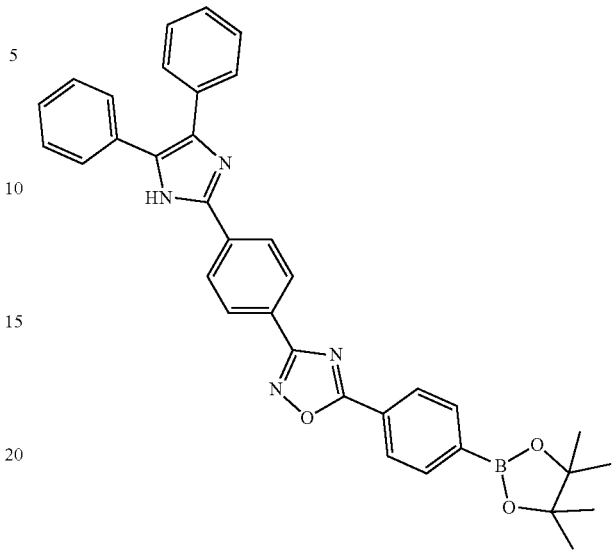

[Chemical Formula 1]

The compound represented by Chemical Formula 1 is 5-(4-(4,4,5,5-tetramethyl-1,3,2-dioxaborolan-2-yl)phenyl)-3-(4-(4,5-diphenyl-1H-imidazol-2-yl)phenyl)-1,2,4-oxadiazole (hereinafter, referred to also as ARBD).

When the citrate detection sensor including the compound represented by Chemical Formula 1 reacts with citrate, a fluorescent color may be expressed. Particularly, the fluorescence wavelength is changed from blue fluorescence to green fluorescence, and thus a green fluorescence color may be expressed.

Figure 1:
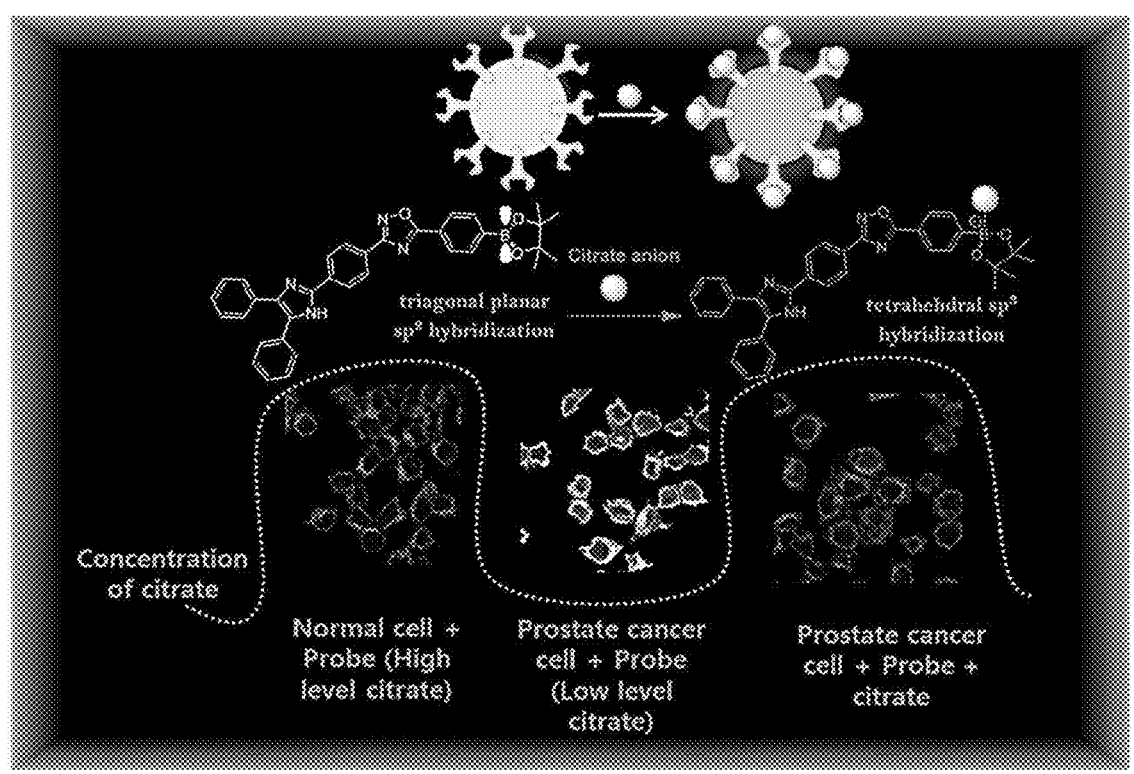
FIG. 1 is a schematic view illustrating a citrate detection mechanism of the citrate detection sensor according to an embodiment.

FIG. 1 illustrates a change in fluorescence color, when the citrate detection sensor including ARBD reacts with citrate.

Referring to FIG. 1, it can be seen that a part of fluorescence in a solution state shows weak blue fluorescence, and increased fluorescence emission appears in an aggregated state referred to as aggregation-induced emission (AIE)/aggregation-enhanced emission (AEE) when ARBD reacts with citrate. In addition, while citrate reacts with the fluorescence sensor, the fluorescence emission intensity shows a red shift and the emission intensity is increased. Particularly, the reaction mechanism herein is expected as follows.

(i) Hydrogen bonding between citrate and —NH proton of a heteroatom in ARBD (ii) Ionic bonding between a negatively charged oxygen atom in citrate and a positively charged boron atom in ARBD (wherein since long conjugation exists over the whole ARBD, the heteroatom causes electron delocalization in the whole molecule to provide positive nature to the boron atom, and thus the boron element is positively charged).

Meanwhile, when the compound represented by Chemical Formula 1 reacts with citrate, the fluorescence intensity in a wavelength range of 400-600 nm may be increased to 450-750 nm. Thus, it is possible to detect citrate by observing a change in fluorescence color and intensity by the naked eyes or a fluorescence photometer (or a fluorescence imaging system such as a confocal system).

According to an embodiment, the citrate detection sensor may have a pH of 6-8, more particularly pH 7. When the citrate sensor has a pH value beyond the above-defined range, the ratio of fluorescence intensity may be decreased to cause insufficient fluorescence.

According to another embodiment, the citrate detection sensor may detect citrate at a temperature ranging from 5° C. to 50° C., more particularly from 20° C. to 37° C. Since citrate may be detected even at room temperature, the citrate detection sensor may have a wide application spectrum.

According to still another embodiment, the citrate detection sensor may provide a citrate detection result within 15 minutes. Thus, the citrate detection sensor is advantageous in that it allows rapid detection.

In addition, the citrate detection sensor may have a detection limit of 10 nM, and thus allows detection of a trace amount of citrate.

According to an embodiment, the citrate detection sensor may be used for detection of citrate in cells, particularly in prostate cells, and more particularly in prostate cancer cells.

In other words, while the citrate concentration in a healthy man body fluid is in a normal range, 50-200 mM, the citrate concentration in prostate cancer tissue cells is reduced to 2-20 mM, which suggests significant progress of prostate cancer. When using the citrate detection sensor disclosed herein, it is possible to detect citrate in prostate cancer tissue cells. In addition, since the citrate detection sensor has a significantly low detection limit, it is possible to determine whether prostate cancer progresses or not with ease.

According to another embodiment, when the citrate detection sensor reacts with citric acid contained in normal cells, it expresses green fluorescence. On the other hand, when the citrate detection sensor reacts with citric acid in prostate cancer cells, it may express blue fluorescence. Particularly, citrate concentration is high in normal cells to express a green fluorescence color. However, when the citrate detection sensor reacts with citric acid in prostate cancer cells, it may express blue fluorescence. In other words, the citrate detection sensor disclosed herein may express blue fluorescence in prostate cancer cells containing a small amount of citrate.

Meanwhile, although there is no particular limitation, the citrate detection sensor may be a paper-strip type sensor including the compound represented by Chemical Formula 1 supported in paper. In this case, it is possible to use such a paper-strip type sensor very conveniently for detection of citrate.

In addition, the citrate detection sensor has selectivity to citrate, and thus may react only with citrate without reaction with hydrogen peroxide ($H_2O_2$), glucose, fructose, sucrose, or the like.

As described above, the citrate detection sensor includes 5-(4-(4,4,5,5-tetramethyl-1,3,2-dioxaborolan-2-yl)phenyl)-3-(4-(4,5-diphenyl-1H-imidazol-2-yl)phenyl)-1,2,4-oxadiazole which causes a red shift of fluorescence emission wavelength and a significant increase in fluorescence intensity. The compound has significantly high selectivity and sensitivity to citrate. Thus, it is possible to detect citrate with ease merely by the naked eyes or by using a fluorescence photometer. Therefore, the citrate detection sensor may be used widely in various fields, such as pharmaceuticals, industrial spots handling chemicals, environmental pollution samples, forensic scientific samples and drinking water.

Prostate Cancer Detection Kit

In another aspect, there is provided a kit for diagnosing prostate cancer which includes a citrate detection sensor compound including a compound represented by the following Chemical Formula 1:

[Chemical Formula 1]

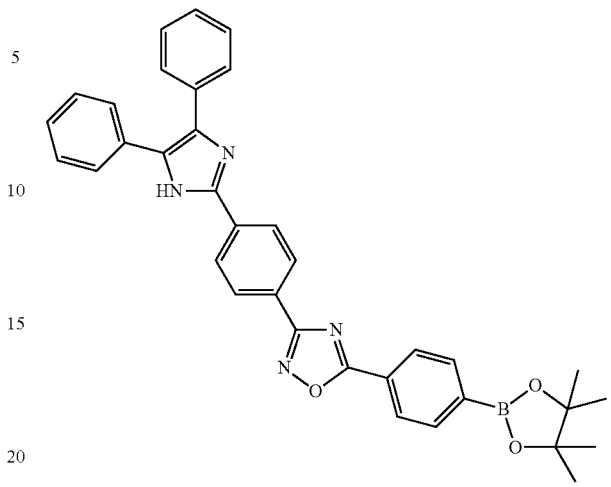

According to an embodiment, the kit for diagnosing prostate cancer may further include a unit for determining concentration in a biological sample isolated from the human body. Therefore, it is possible to carry out determination of concentration in the body fluid and/or blood isolated from the human body. Herein, when the concentration of citrate is significantly decreased as compared to the normal control, it is possible to diagnose prostate cancer or potential prostate cancer.

According to another embodiment, the unit for determining concentration in a biological sample may further include instructions including a method for diagnosing prostate cancer, wherein the instructions may include a screening method of diagnosing prostate cancer or potential prostate cancer, when the citrate concentration in at least one of the body fluid and blood analyzed from the unit for determining concentration in a biological sample is reduced to less than ¹⁄₁₀ (i.e., 2-20 mM) of the citrate concentration (50-200 mM) in the normal control.

According to still another embodiment, the unit for determining concentration in a biological sample may further include instructions including a method for diagnosing prostate cancer, wherein the instructions may include a screening method of diagnosing prostate cancer or potential prostate cancer, when the citrate detection sensor expresses blue fluorescence as compared to the normal control after the sensor reacts with at least one of the body fluid and blood analyzed from the unit for determining concentration in a biological sample.

Thus, it is possible to diagnose prostate cancer or potential prostate cancer with ease by using the kit for diagnosing prostate cancer.

Method for Detecting Citrate Using Citrate Detection Sensor

In still another aspect, there is provided a method for detecting citrate which includes: preparing a citrate detection sensor including a compound represented by the following Chemical Formula 1; allowing the citrate detection sensor to react with a sample to be analyzed; and determining a change in fluorescence of the citrate detection sensor after the citrate detection sensor reacts with the sample to be analyzed to detect citrate:

[Chemical Formula 1]

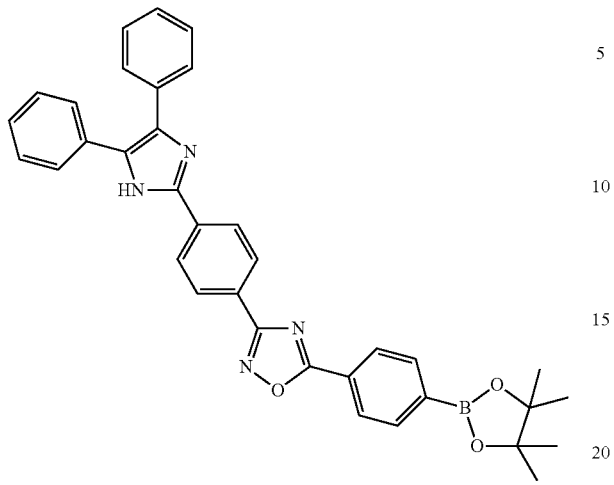

[Chemical Formula 1]

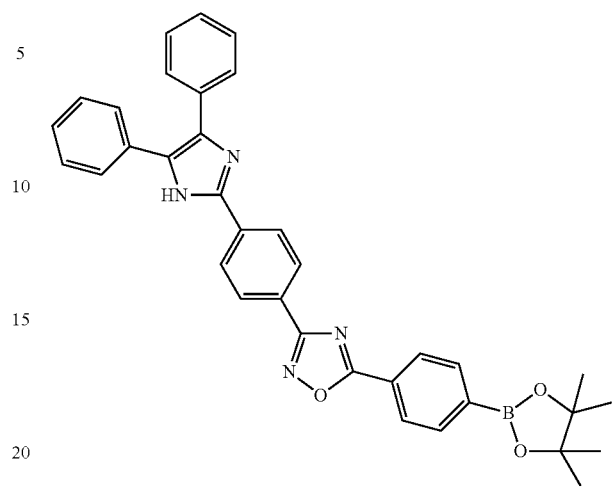

According to an embodiment, the allowing the sensor to react with the sample to be analyzed may include: introducing the sensor and the sample to be analyzed to a reaction chamber; controlling pH in the reaction chamber; and allowing the sensor to react with the sample to be analyzed in the reaction chamber.

According to another embodiment, pH in the reaction chamber may be controlled to 6-8.

According to still another embodiment, the sample to be analyzed may include at least one of the body fluid and blood in the human body.

According to yet another embodiment, the sample to be analyzed which reacts with the citrate detection sensor may include at least one of the body fluid and blood in prostate cancer cells.

Thus, detection of citrate using the citrate detection sensor may be carried out through a very simple process. Therefore, since the compound has significantly high selectivity and sensitivity to citrate, it is possible to detect citrate with ease merely by the naked eyes and/or by using a fluorescence photometer. As a result, the citrate detection sensor may be used widely in various industrial fields.

Hereinafter, the present disclosure will be described with respect to the specific embodiments. However, it will be apparent to those skilled in the art that these exemplary embodiments are provided for illustrative purposes only and the following examples are not intended to limit the scope of the present disclosure.

EXAMPLES

Example 1: Synthesis of Compound Represented by [Chemical Formula 1]

The compound represented by Chemical Formula 1, 5-(4-(4,4,5,5-tetramethyl-1,3,2-dioxaborolan-2-yl)phenyl)-3-(4-(4,5-diphenyl-1H-imidazol-2-yl)phenyl)-1,2,4-oxadiazole (hereinafter, also referred to as ARBD) was prepared as follows.

Diphenylethanedione (or benzyl) (1) was added to 4-cyanobenzaldehyde (2) in the presence of ammonium acetate. The resultant 4-(4,5-diphenyl-1H-imidazol-2-yl)benzonitrile (3) was allowed to react with hydroxylamine hydrochloride to obtain N'-hydroxy-4-(4,5-diphenyl-1H-imidazol-2-yl)benzamidine (4). Then, 4-bromo benzoic acid (5) was allowed to react with bis(pinacolato)diboron (6) to obtain 4-carboxyphenylboronic acid pinacol ester (7). Finally, N-hydroxy-4-(4,5-diphenyl-1H-imidazol-2-yl)benzamidine was allowed to react with 4-carboxyphenylboronic acid pinacol ester (7) to obtain 5-(4-(4,4,5,5-tetramethyl-1,3,2-dioxaborolan-2-yl)phenyl)-3-(4-(4,5-diphenyl-1H-imidazol-2-yl)phenyl)-1,2,4-oxadiazole (hereinafter, also referred to as ARBD).

[Reaction Scheme 1]

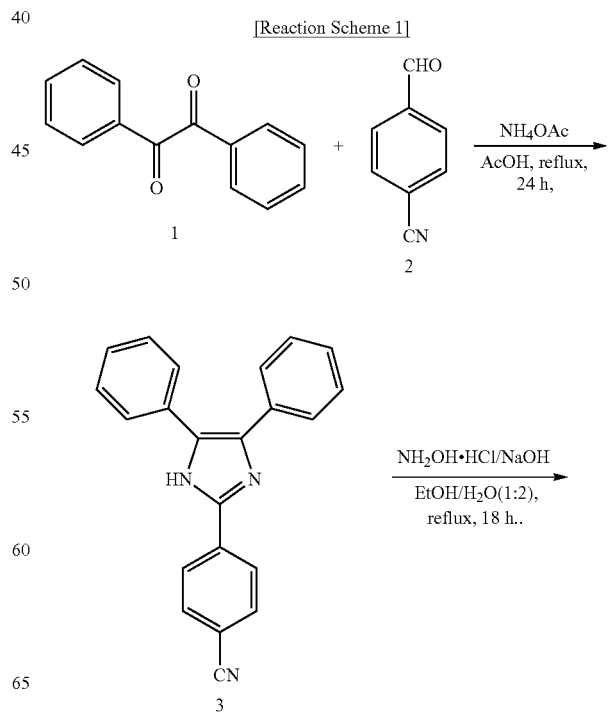

-continued

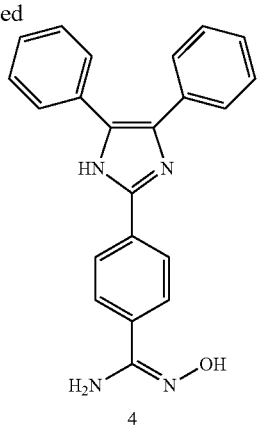

4

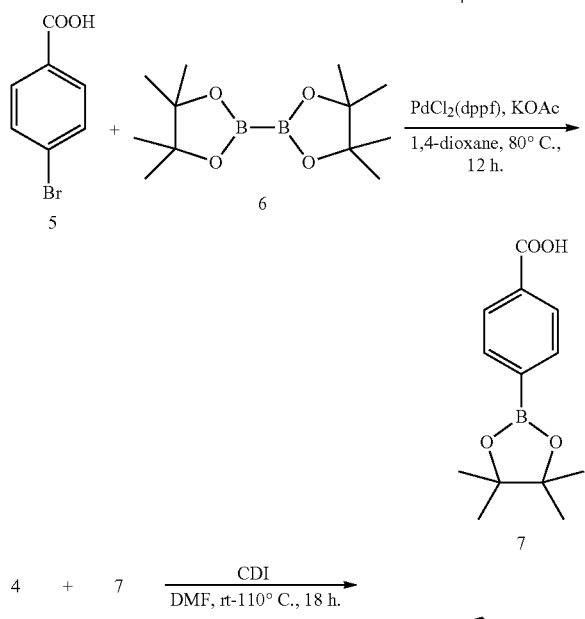

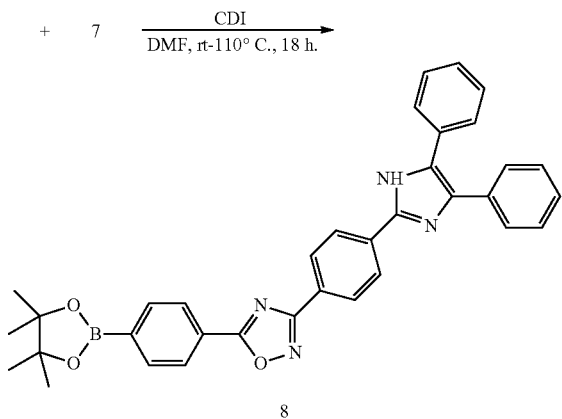

Test Example 1: Reaction Mechanism of ARBD with Citrate

To demonstrate the reaction mechanism of ARBD with citrate, ARBD was subjected to $^1$H NMR titration. After ARBD was allowed to react with 0.5, 1.0, 1.5 and 2.0 equivalents of citrate, $^1$H NMR titration of ARBD was carried out in DMSO-$d_6$. The results are shown in FIG. 2.

Figure 2:
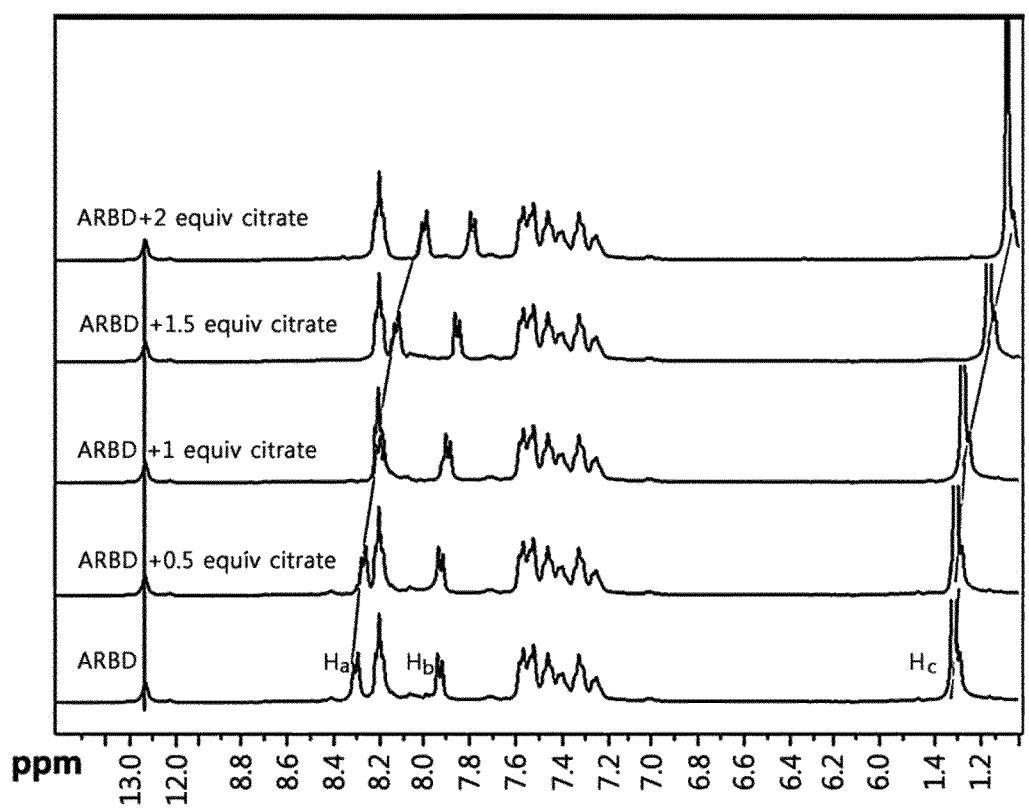
FIG. 2 is a graph illustrating changes in the $^1$H NMR (400 MHz) spectrum of citrate, after the citrate detection sensor reacts with different equivalents of citrate.

Referring to FIG. 2, it can be seen that ARBD shows phenyl rings Ha and Hb (δ 8.30 and 7.94 ppm) bound with a boron element and boronate methyl ester proton Hc (δ 1.32 ppm). In addition, when the concentration of citrate is increased, the peaks of phenyl hydrogen attached to boron and boronate methyl ester show a clear shift to the upfield. When 0.5 eq of citrate is added to ARBD, the typical phenyl peak undergoes a shift to the upfield and is observed at δ 8.28 ppm (Ha) and 7.93 ppm (Hb). It can be also seen that a singlet peak of methyl ester appears at δ 1.30 ppm (Hc). It can be clearly seen that phenyl Ha and Hb (δ 8.26 ppm and 7.92 ppm) and methyl ester Hc (δ 1.26 ppm) still undergo a shift to the upfield, after adding 1.0 eq. of citrate to ARBD. When adding 1.5 eq of citrate to ARBD, typical phenyl peaks are observed at δ 8.22 ppm (Ha) and 7.91 ppm (Hb), and methyl ester appears at δ 1.26 ppm (Hc). In addition, when the concentration of citrate is increased to 2.0 eq, phenyl and methyl ester appear at δ 8.17 (Ha) and 7.88 (Hb), and 1.14 ppm (Hc), respectively.

Further, it can be seen that the hydrogen adjacent to the boron element undergoes a shift but the imidazole-NH hydrogen undergoes no shift during the addition of citrate. This suggests that the detection path is ionic interaction between citrate and boron in ARBD (boron energy in ARBD: +1.15 eV). The boron in the boronate moiety functions as a Lewis acid and accepts electrons from citrate by using a vacant 'p' orbital with sp$^2$ hybridization. The negatively charged citrate ion easily donates electrons and functions as a Lewis base. The electron shift from citrate to the vacant 'p' orbital of boron causes hybridization from a sp$^2$ triangular planar structure to a sp$^3$ tetrahedral structure. After a conjugate having an ARBD-citrate complex structure, the polarity of ARBD is increased. This is because the energy gap between the donator (citrate) and the receptor (ARBD) is decreased through the formation of a local excitation state of the charge-transferred complex (citrate-ARBD) (increased fluorescence emission intensity mainly belongs to the AIE mechanical path).

Then, as the concentration of citrate is increased, a lower energy emission spectrum was observed with a larger wavelength.

Test Example 2: Citrate Detection Sensor Including ARBD and Chemical Stoichiometry and Rate Constant for Reaction of Citrate To understand the bonding behavior in the reaction between the citrate detection sensor including ARBD and citrate, the reaction was investigated by using the Job plot. The data are shown in FIG. 3.

Figure 3:
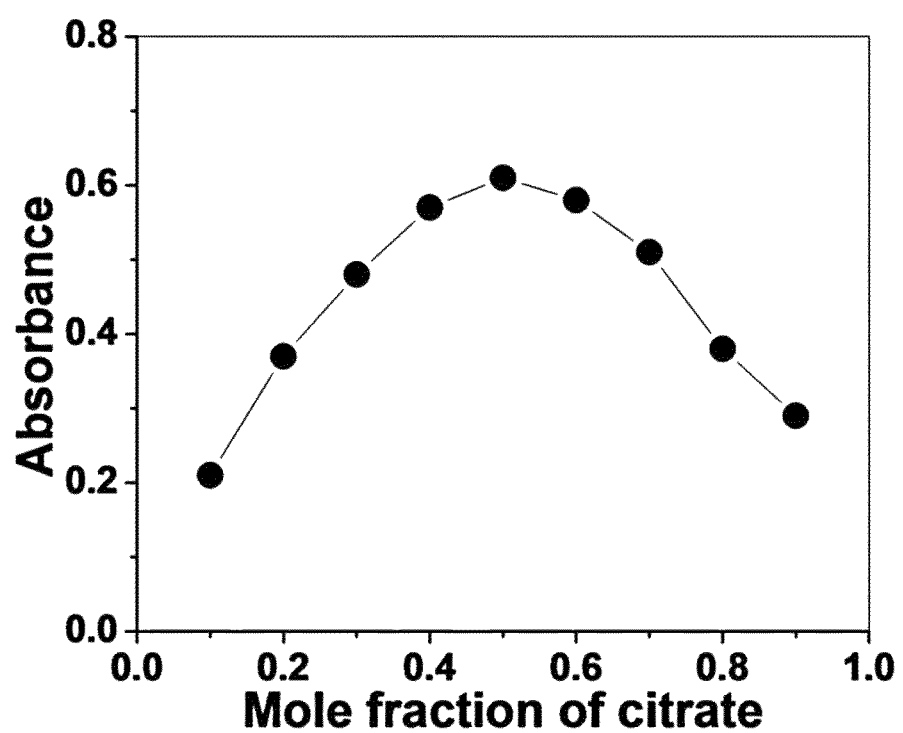
FIG. 3 is a graph illustrating the Job plot of the absorbance of 5-(4-(4,4,5,5-tetramethyl-1,3,2-dioxaborolan-2-yl)phenyl)-3-(4-(4,5-diphenyl-1H-imidazol-2-yl)phenyl)-1,2,4-oxadiazole (hereinafter, referred to also as ARBD) as a function of the mole fraction of citrate.
Figure 4:
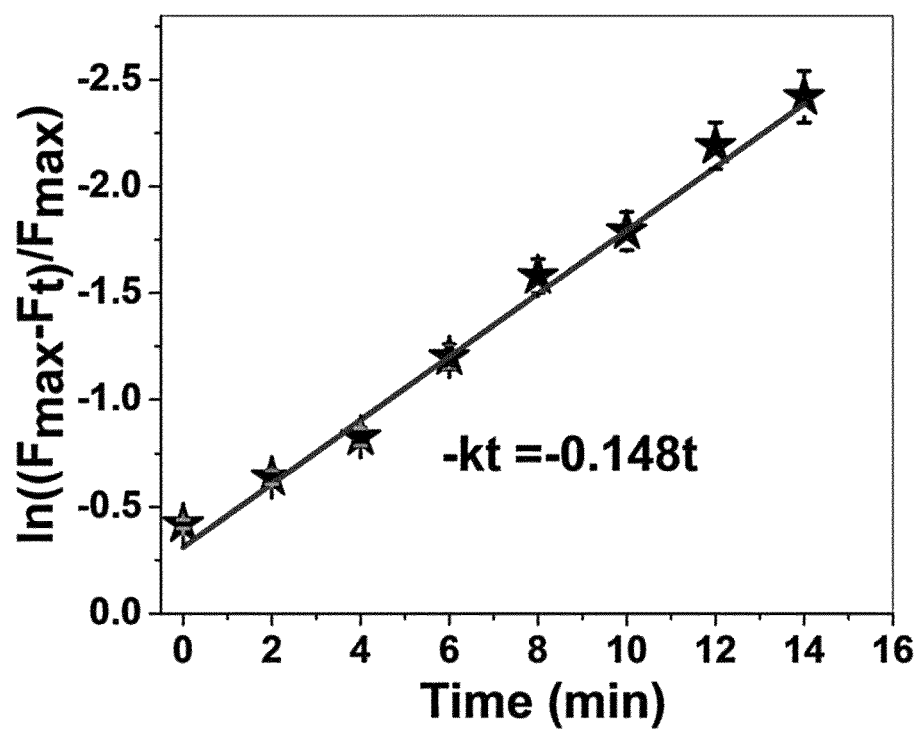
FIG. 4 is a graph illustrating the fluorescence intensity as a function of time when the citrate detection sensor reacts with citrate.

It can be seen from FIG. 3 that the maximum absorption intensity appears at a molar fraction of 0.5. Thus, it can be seen that a 1:1 complex is formed during the reaction of the citrate detection sensor with citrate. In this case, the reaction kinetics may be expressed by $-kt=\ln(F_{max}-F)/F_{max}$ (wherein k=rate constant, and 'F' and '$F_{max}$' represent the fluorescence intensity at time 't'). In addition, the maximum intensity reaction value accomplished after the completion of the reaction was calculated by using the plot of '$\ln(F_{max}-F)/F_{max}$ vs time' as shown in FIG. 4. As a result, it can be seen that the value of k (reaction rate constant) is 0.148 min$^{-1}$. Therefore, the reaction between the citrate detection sensor including ARBD and citrate shows a rate constant of 0.148 min$^{-1}$. This suggests that the reaction activation energy may be relatively high.

Figure 5:
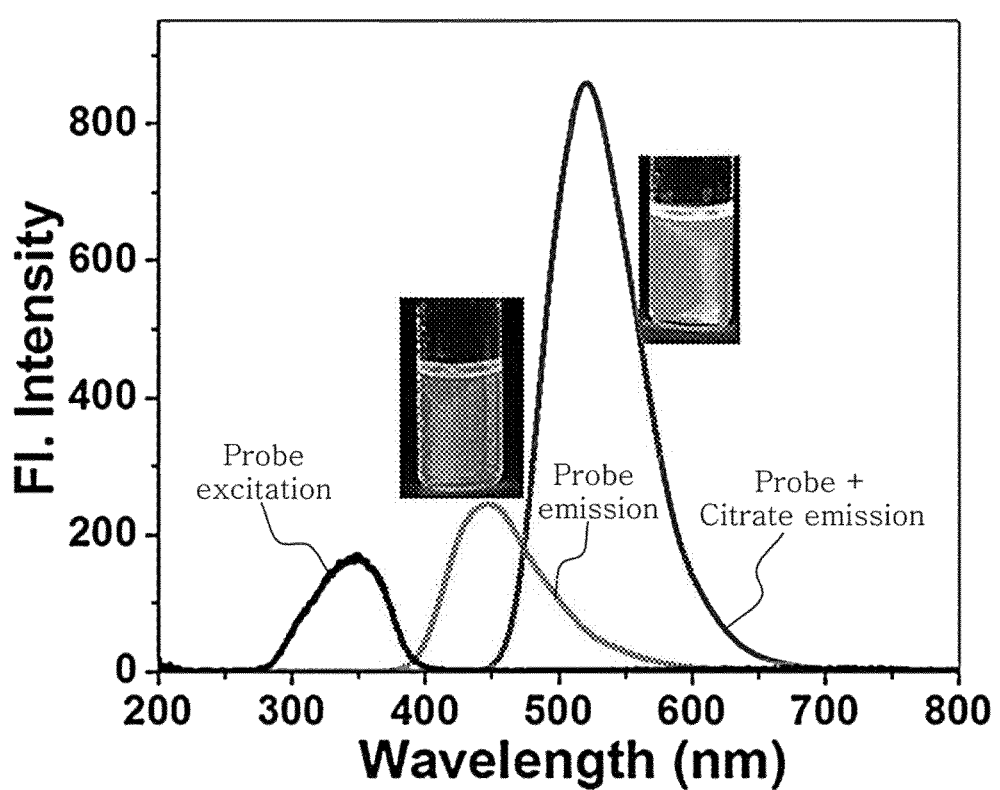
FIG. 5 is a graph illustrating a fluorescence emission spectrum of ARBD and fluorescence excitation and emission wavelengths depending on the reaction with citrate.

Meanwhile, referring to FIG. 5, it can be seen that the citrate detection sensor not subjected to reaction with citrate expresses (blue) fluorescence while emitting weak fluorescence at 346 nm and 458 nm. On the contrary, when citrate is added to the citrate detection sensor including 2 µM of ARBD in the presence of 10 mM of 4-(2-hydroxyethyl)-1- piperazineethane sulfonic acid (HEPES) buffer (2 vol % DMSO) at pH 7.4, it can be seen that strong fluorescence appears at 548 nm together with a dramatic color change from blue to green. Table 1 shows the photophysical properties of the citrate detection sensor in the presence and absence of citrate. However, such a change in fluorescence is differentiated preferentially by visualization.

TABLE 1

Change in Fluorescence after Reaction of ARBD with citrate

| Compound | Maximum absorption wavelength ($\lambda_{abs}$) | Maximum emission wavelength ($\lambda_{emiss}$) | Fluorescence quantum yield |
|---|---|---|---|
| ARBD | 352 | 458 | 0.18 |
| ARBD + citrate | 352 | 548 | 0.51 |

Figure 6A:
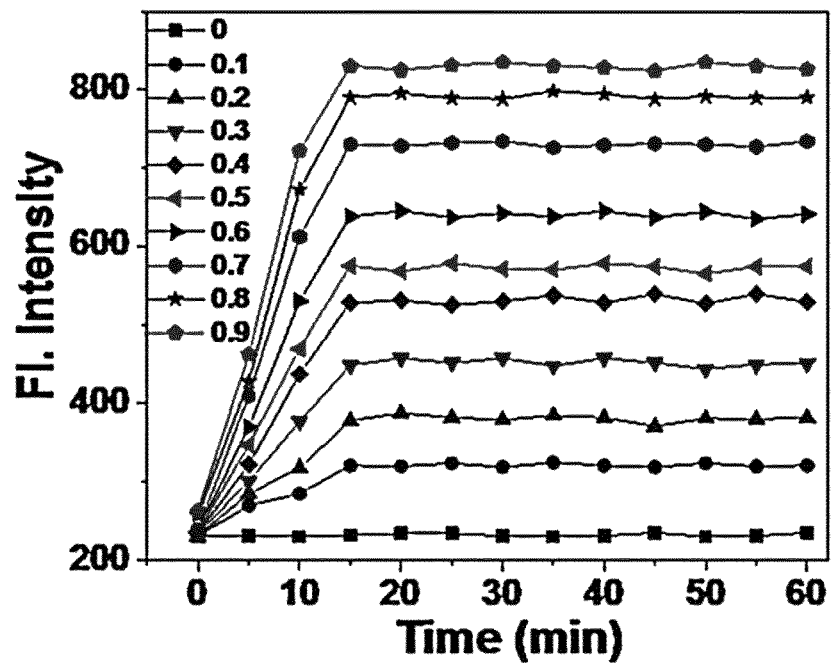
FIG. 6A to FIG. 6C show a graph illustrating a change in fluorescence intensity of the citrate detection sensor as a function of time in the presence of different concentrations of citrate (0-0.9 μM), a graph illustrating fluorescence emission intensity of ARBD and citrate at different pH values and a fluorescence image thereof, respectively.
Figure 6B:
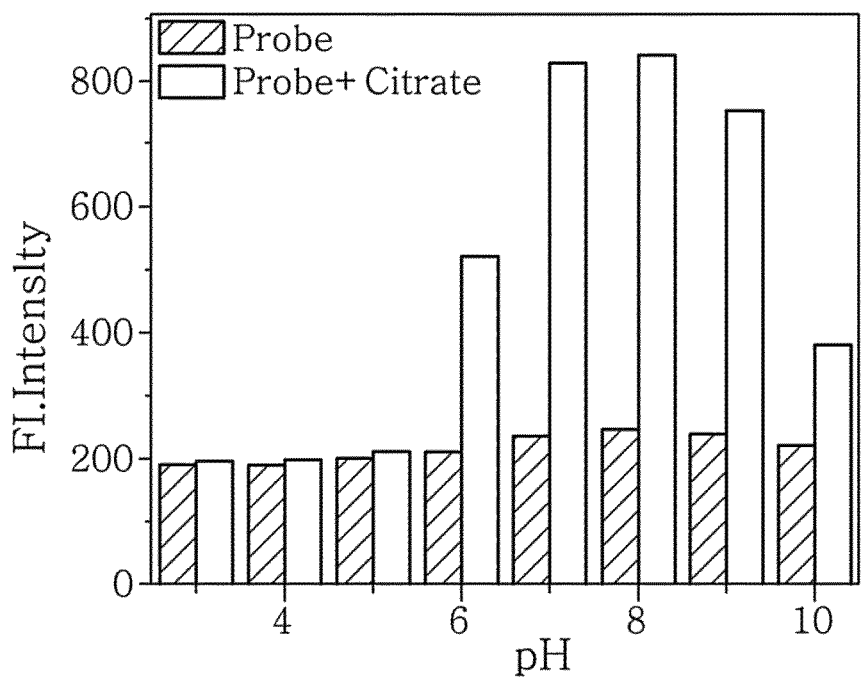
Figure 6C:
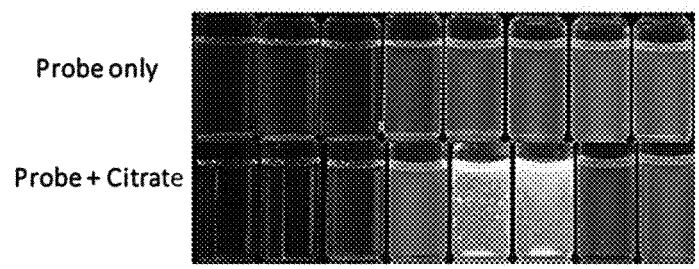

Meanwhile, FIG. 6A to FIG. 6C show a graph illustrating a change in fluorescence intensity of the citrate detection sensor as a function of time in the presence of different concentrations of citrate (0-0.9 μM), a graph illustrating fluorescence emission intensity of ARBD and citrate at different pH values and a fluorescence image thereof, respectively.

When optimizing the determination condition in FIG. 6A, it can be seen that the maximum value of fluorescence intensity is accomplished within about 15 minutes. It can be also seen that the fluorescence intensity is maintained constantly to 60 minutes, and the sensor itself is retained constantly and shows high stability once it react with citrate over the whole concentration ranges. Referring to FIG. 6B and FIG. 6C, the fluorescence intensity of the citrate detection sensor is not affected by pH substantially but shows the highest and stable fluorescence intensity at about pH 7-8. Thus, it can be seen that when citrate is introduced to the citrate detection sensor, fluorescence enhancement may be varied with pH.

Figure 7A:
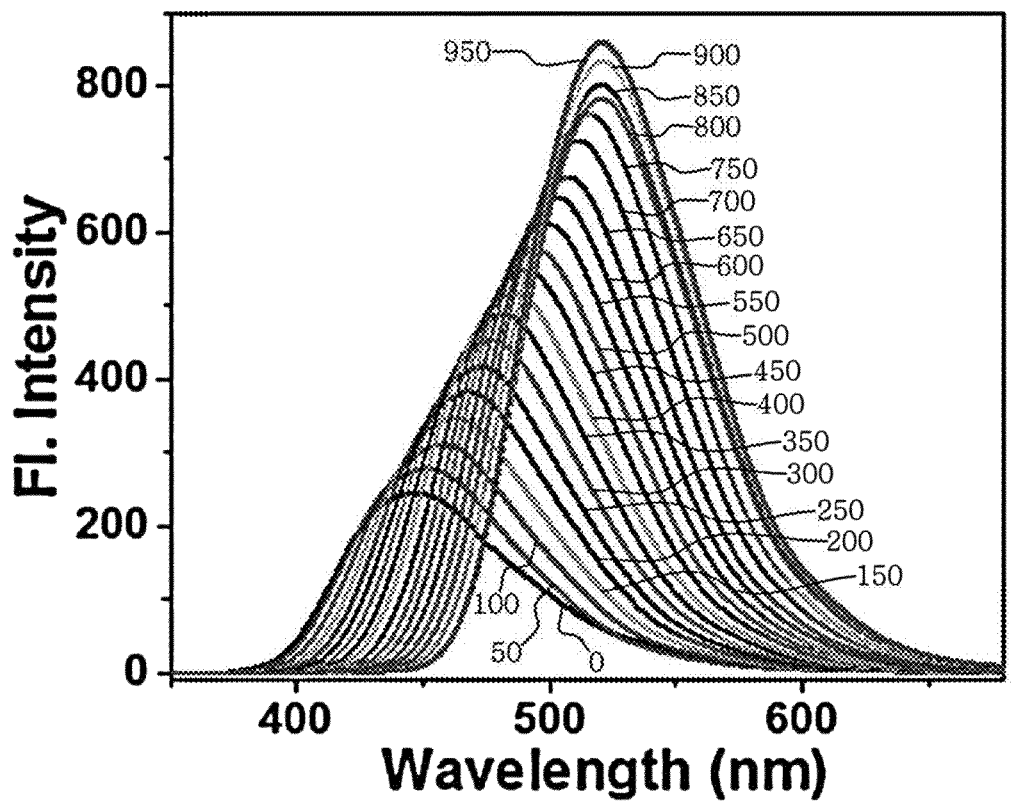
FIG. 7A to FIG. 7C show a fluorescence reaction spectrum of the citrate detection sensor, a calibration curve of fluorescence intensity as a function of concentration of citrate and a fluorescence image, when applying different concentrations of citrate, respectively.
Figure 7B:
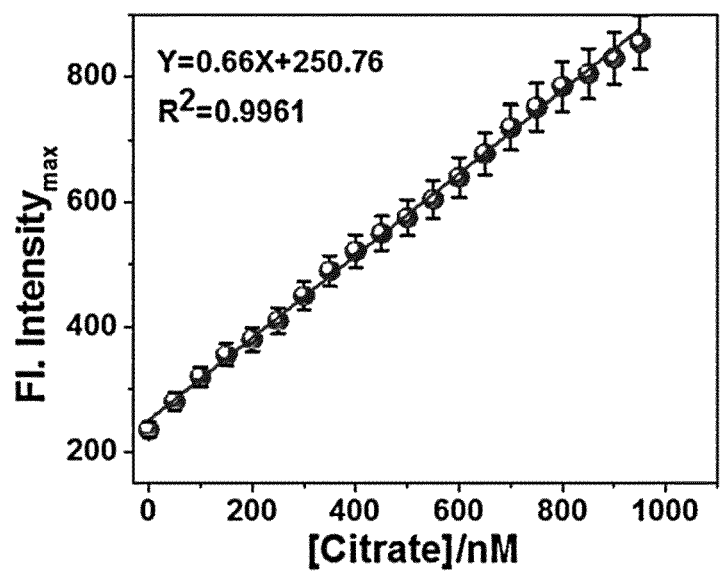
Figure 7C:
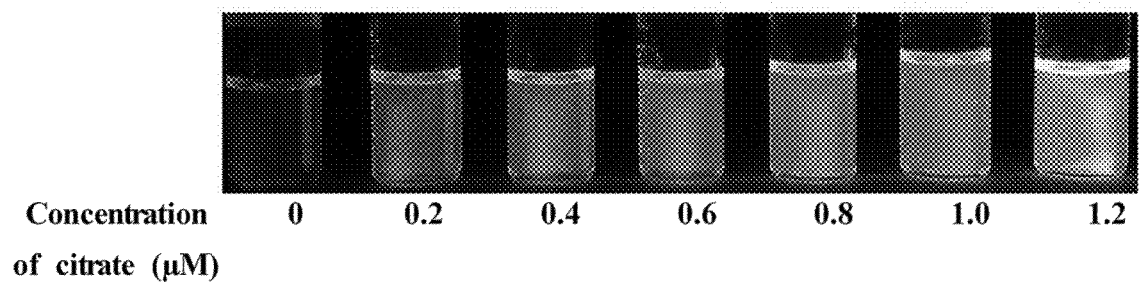

Test Example 3: High-Sensitivity Detection of Citrate Using Reaction Mechanism of Citrate Detection Sensor with Citrate The initial citrate tracking ability of the citrate detection sensor including ARBD was evaluated by using UV-Vis absorption spectrometry using ARBD at pH 7.4 in the presence of 10 mM of HEPES buffer solution (2 vol % DMSO). Referring to FIG. 7A to FIG. 7C, it is possible to determine a change in fluorescence spectrum of ARBD when adding citrate at a concentration increasing linearly. Particularly, it can be seen that ARBD shows an absorption peak at 346 nm at the initial stage, and the absorption spectrum shows a change whenever 1 μM of citrate is added from 0 to 12 μM. The absorption intensity at 346 nm is decreased whenever citrate is added and a new peak position appears at 400 nm. In addition, as shown in FIG. 7A to FIG. 7C, it can be seen that an increase in concentration of citrate affects both the fluorescence intensity and the fluorescence wavelength. Further, it can be seen that when the concentration of citrate is increased from 0 to 800 nM for the citrate detection sensor including 2 μM of ARBD at pH 7.4 in the presence of 10 mM of HEPES buffer solution (2 vol % DMSO), the maximum fluorescence intensity is increased linearly to 548 nm. It can be also seen that when the concentration of citrate is increased to 950 nM, the peak at 548 nm is increased linearly while causing no change in wavelength. Herein, it is shown that the calibration curve is Y=0.66 X+250.76 ($R^2$=0.9961) and the detection limit is 10 nM (S/N=3), which is significantly improved as compared to the related art.

Figure 8A:
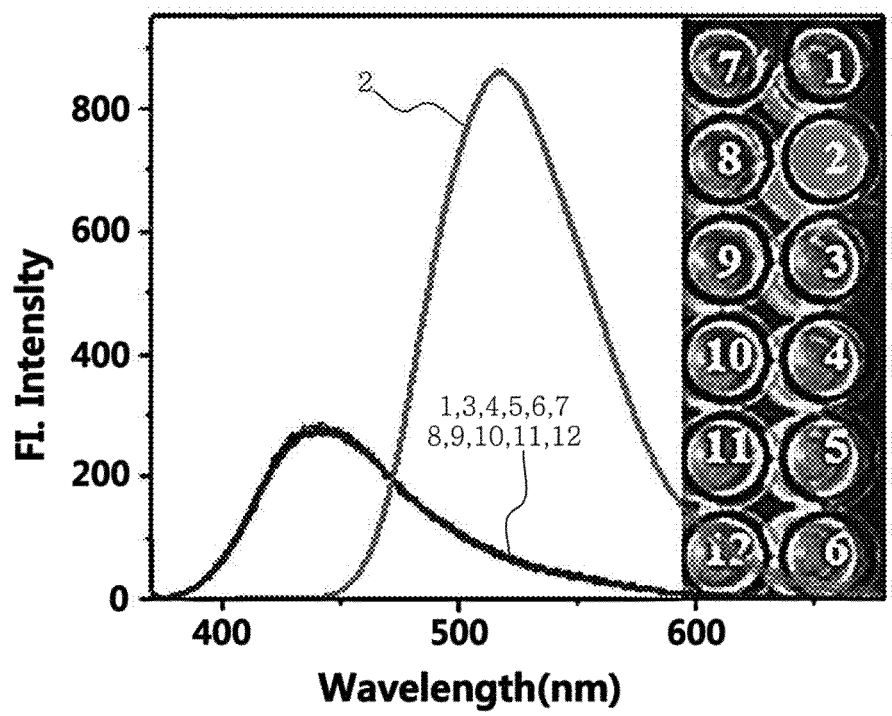
FIG. 8A to FIG. 8C are graphs illustrating the selectivity and interference of the citrate detection sensor for detecting citrate.
Figure 8B:
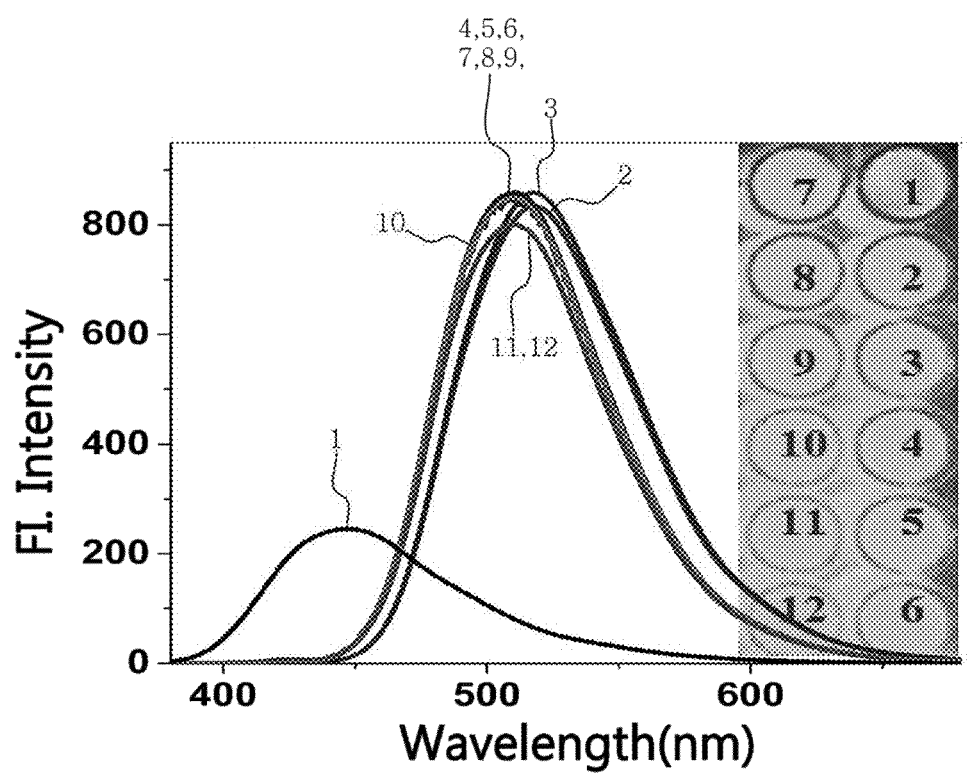
Figure 8C:
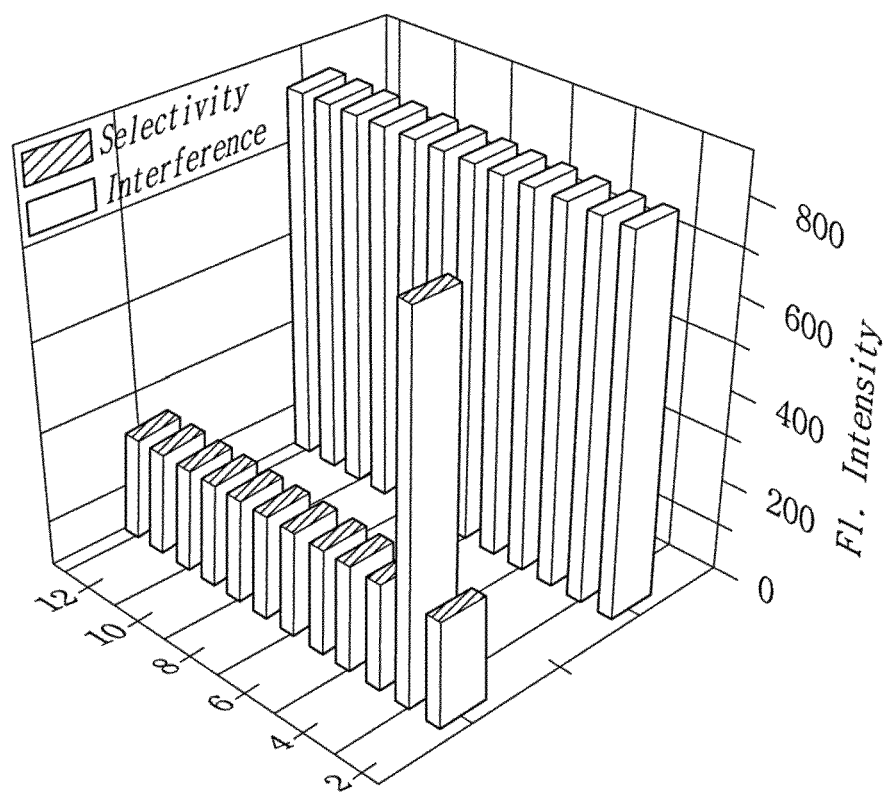

Test Example 4. Selectivity and Interference of Citrate Detection Sensor for Detection of Citrate The citrate detection sensor was used to test the selectivity and interference capability to the related similar species for the detection of the other biological carboxylate and citrate. The results are shown in FIG. 8A to FIG. 8C. For this test, 1 μM of citrate and 0.5 mM of the other ions were added ((1) sensor, (2) citrate, (3) fumarate, (4) benzoate, (5) glutamate, (6) succinate, (7) malonate, (8) oxalate, (9) acetate, (10) phosphate, (11) sulfite, and (12) sulfate). In FIG. 8A, it is shown that only citrate can induce fluorescence enhancement unlike the other species. Moreover, it can be seen that even when the other species of ionic compounds have a concentration at least 500 times higher than the concentration of citrate, there is no effect upon the detection of citrate (FIG. 8B).

FIG. 8C shows the selectivity and interference capability of the citrate detection sensor. Referring to FIG. 8C, it can be seen that even when the other ionic substances have a concentration at least 500 times higher than the concentration of citrate, the citrate detection sensor is reactive selectively with citrate without any interference under high sensitivity. In addition, since it is well known that boronate is a diol sensor, selectivity was also determined for the other materials having a diol moiety, such as hydrogen peroxide ($H_2O_2$), glucose, fructose, sucrose, dopamine species, or the like. However, it can be seen that the citrate detection sensor reacts only with citrate and hydrogen peroxide. Although the two analytes undergo a reaction in response to the fluorescence intensity, it can be seen that citrate emits green fluorescence and $H_2O_2$ emits blue fluorescence. Thus, it can be seen that since only citrate emits green fluorescence in a biological sample at a concentration of 'μM' scale, it is possible to detect citrate with ease by the naked eyes through the citrate detection sensor.

Test Example 5: Fluorescence Expression of Citrate Detection Sensor in Living PC3 Cells The citrate detection sensor was evaluated in terms of its probe capability in living cells (PC3). The results are shown in FIG. 9A to FIG. 9F. This is because the citrate detection sensor disclosed herein shows high measurement sensitivity (nM scale) for the detection of citrate only emitting green fluorescence, and thus it is thought that the citrate detection sensor allows tracking of presence/absence of citrate in cell lines. Particularly, after the citrate sensor including ARBD (2 μM) was cultured for 30 minutes, the image in PC3 cells was observed.

Figure 9A:
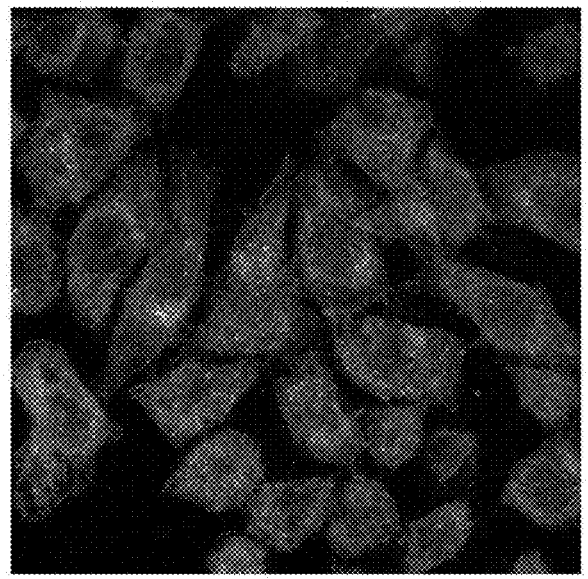
FIG. 9A to FIG. 9F are an image illustrating the fluorescence obtained when ARBD is introduced to prostate cancer cell lines.
Figure 9B:
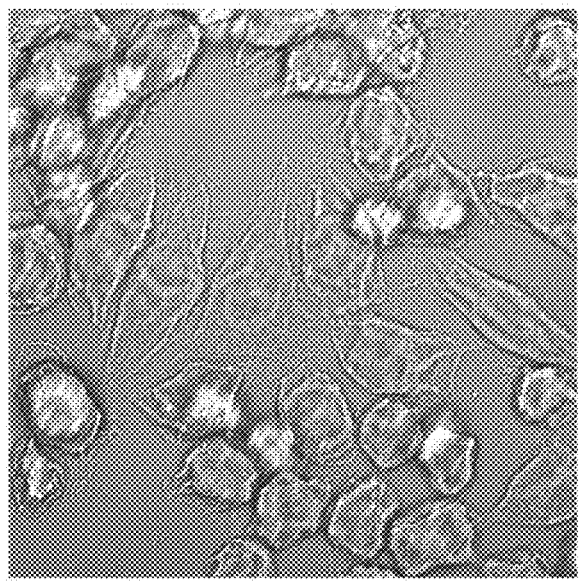
Figure 9C:
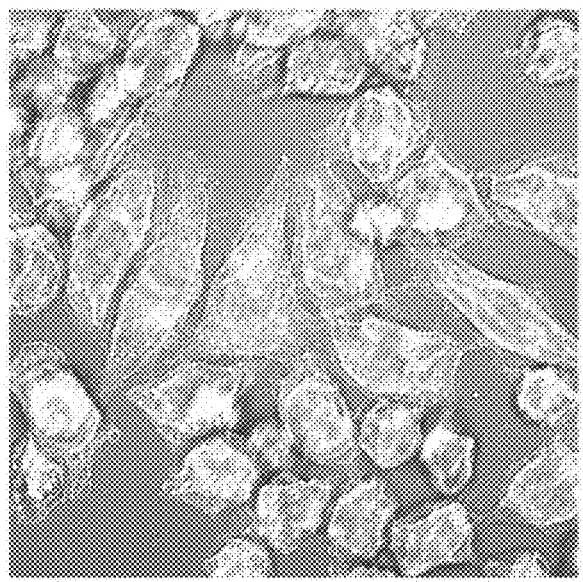
Figure 9D:
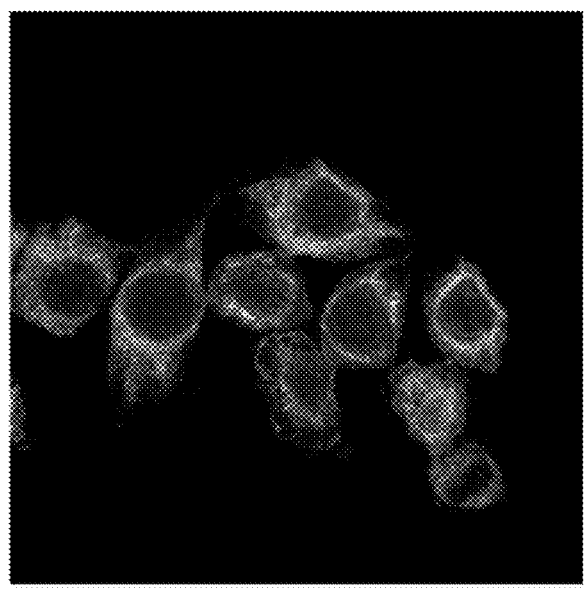
Figure 9E:
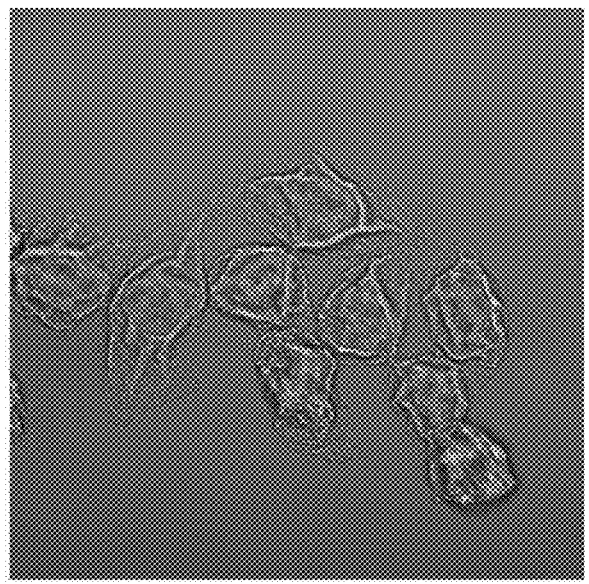
Figure 9F:
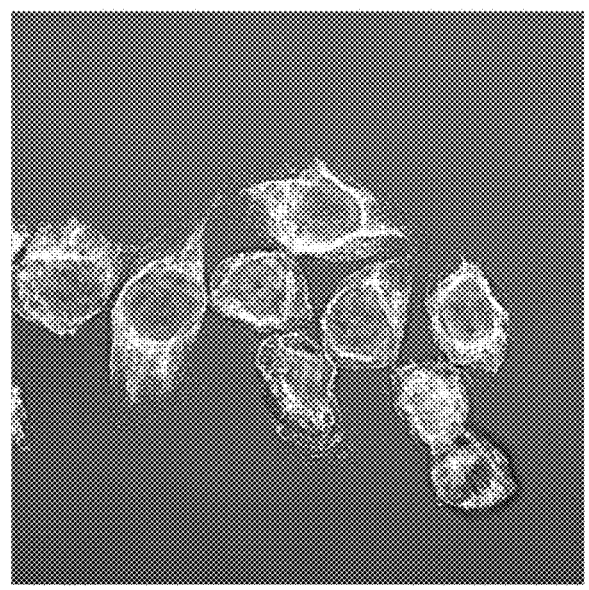

FIG. 9A to FIG. 9C show the fluorescence expressed generally when ARBD is introduced to prostate cancer cells. The image (FIG. 9C) of the expressed fluorescence (FIG. 9A) overlapped with the photo image (FIG. 9B) of the cell lines is shown between them. Then, green fluorescence expressed when adding citrate to the detection sensor inserted to the cell lines was observed. The image (FIG. 9D) after adding citrate, the photo image (FIG. 9E) thereof and their overlapped image (FIG. 9F) are shown in FIG. 9D to FIG. 9F.

What is claimed is:

1. A citrate detection sensor comprising a compound represented by the following Chemical Formula 1:

[Chemical Formula 1]

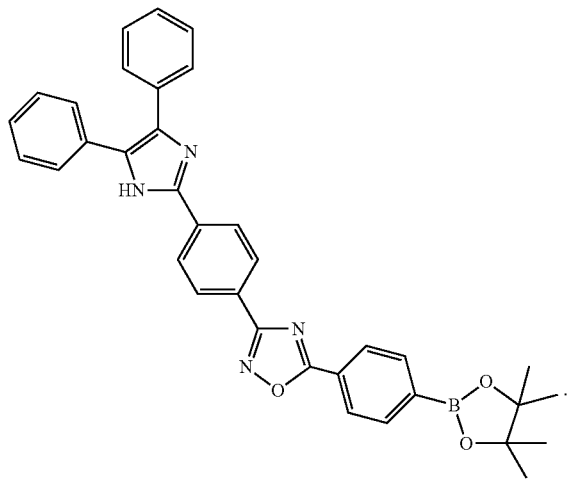

2. The citrate detection sensor according to claim 1, wherein the compound represented by Chemical Formula 1 expresses a green fluorescence color through the reaction with citrate.

3. The citrate detection sensor according to claim 1, wherein the fluorescence intensity in a wavelength range of 400-450 nm is increased to 450-700 nm, when the compound represented by Chemical Formula 1 reacts with citrate.

4. The citrate detection sensor according to claim 1, which has a pH controlled to 6-8.

5. The citrate detection sensor according to claim 1, which detects citrate at 20-37° C.

6. The citrate detection sensor according to claim 1, which shows a citrate detection result within 15 minutes.

7. The citrate detection sensor according to claim 1, which has a detection limit of 10 nM.

8. The citrate detection sensor according to claim 1, which is used to detect citrate in cells.

9. The citrate detection sensor according to claim 8, which is used to detect citrate in prostate cancer cells.

10. The citrate detection sensor according to claim 1, which is a paper-strip type sensor comprising the compound represented by Chemical Formula 1 supported in paper.

11. A kit for diagnosing prostate cancer which comprises a citrate detection sensor comprising a compound represented by the following Chemical Formula 1:

[Chemical Formula 1]

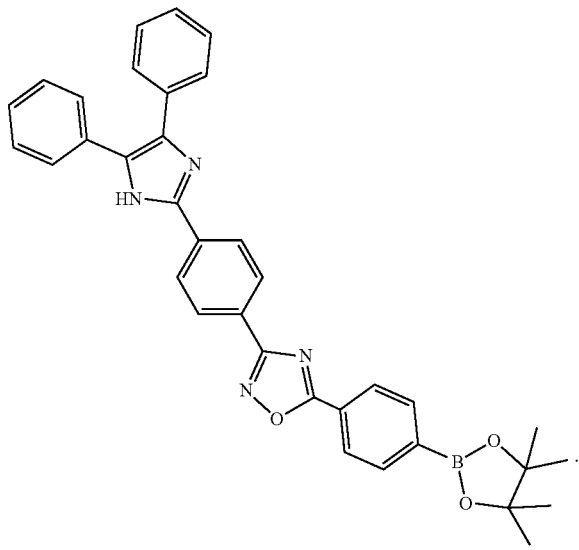

12. The kit for diagnosing prostate cancer according to claim 11, which further comprises a unit for determining concentration in a biological sample isolated from the human body, wherein the unit for determining concentration in a biological sample further comprises the citrate detection sensor.

13. The kit for diagnosing prostate cancer according to claim 12, wherein the unit for determining concentration in a biological sample further comprises instructions comprising a method for diagnosing prostate cancer, and the instructions comprises a screening method of diagnosing prostate cancer or potential prostate cancer, when the citrate concentration in at least one of the body fluid and blood analyzed from the unit for determining concentration in a biological sample is reduced to less than $\frac{1}{10}$ of the citrate concentration in the normal control.

14. The kit for diagnosing prostate cancer according to claim 12, wherein the unit for determining concentration in a biological sample further comprises instructions comprising a method for diagnosing prostate cancer, and the instructions comprises a screening method of diagnosing prostate cancer or potential prostate cancer, when the citrate detection sensor expresses blue fluorescence as compared to the normal control after the sensor reacts with at least one of the body fluid and blood analyzed from the unit for determining concentration in a biological sample.

15. A method for detecting citrate which comprises:
preparing a citrate detection sensor comprising a compound represented by the following Chemical Formula 1;
allowing the citrate detection sensor to react with a sample to be analyzed; and
determining a change in fluorescence of the citrate detection sensor after the citrate detection sensor reacts with the sample to be analyzed to detect citrate:

[Chemical Formula 1]

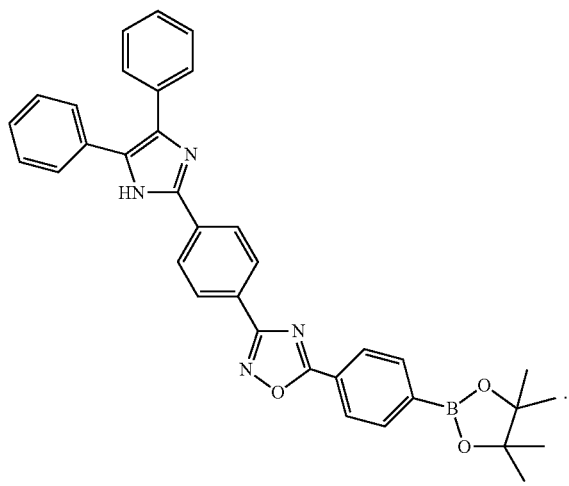

16. The method for detecting citrate according to claim 15, wherein the allowing the sensor to react with the sample to be analyzed comprises:

introducing the sensor and the sample to be analyzed to a reaction chamber;

controlling pH in the reaction chamber; and allowing the sensor to react with the sample to be analyzed in the reaction chamber.

17. The method for detecting citrate according to claim 15, wherein pH in the reaction chamber is controlled to 6-8.

18. The method for detecting citrate according to claim 15, wherein the sample to be analyzed comprises at least one of the body fluid and blood in the human body.

19. The method for detecting citrate according to claim 18, wherein the sample to be analyzed which reacts with the citrate detection sensor comprises at least one of the body fluid and blood in prostate cancer cells.

* * * * *